(12) United States Patent
Haemmerich et al.

(10) Patent No.: US 7,367,974 B2
(45) Date of Patent: May 6, 2008

(54) ELECTRODE ARRAY FOR TISSUE ABLATION

(75) Inventors: Dieter Haemmerich, Madison, WI (US); David M. Mahvi, Middleton, WI (US); John G. Webster, Madison, WI (US); David J. Schutt, Marinette, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 463 days.

(21) Appl. No.: 10/945,380

(22) Filed: Sep. 20, 2004

(65) Prior Publication Data

US 2006/0064084 A1 Mar. 23, 2006

(51) Int. Cl.
*A61B 18/18* (2006.01)
(52) U.S. Cl. .......................... 606/41; 128/898
(58) Field of Classification Search ............ 606/27–52; 128/898
See application file for complete search history.

(56) References Cited

U.S. PATENT DOCUMENTS 6,312,426 B1 11/2001 Goldberg et al.

| 2002/0022864 A1 | 2/2002 | Mahvi et al. |
| 2002/0111615 A1 | 8/2002 | Cosman et al. |
| 2002/0120261 A1 | 8/2002 | Morris et al. |
| 2002/0156472 A1 | 10/2002 | Lee et al. |
| 2004/0039429 A1 | 2/2004 | Daniel et al. |
| 2004/0181216 A1 | 9/2004 | Kelly et al. |
| 2004/0230187 A1 | 11/2004 | Lee et al. |
| 2006/0015095 A1 | 1/2006 | Desinger et al. |

FOREIGN PATENT DOCUMENTS

DE 102 24 154 A 1 5/2002

OTHER PUBLICATIONS

Author: D. Haemmerich, D. J. Schutt, J. A. Will, R. M. Striegel, J. G. Webster, D. M. Mahvi, et al., A Device for Radiofrequency Assisted Hepatic Resection, from Proceedings of the 26th Annual International Conference of the IEEE EMBS, San Francisco, CA, Sep. 1-5, 2004.

Jean-Christophe Weber, MD, et al., New Technique for Liver Resection Using Heat Coagulative Necrosis, Advances in Surgical Technique, Annals of Surgery, vol. 236, No. 5, 560-563, 2002 Lippincott Williams & Wilkins, Inc.

*Primary Examiner*—Roy D. Gibson
*Assistant Examiner*—Pete Vrettakos
(74) *Attorney, Agent, or Firm*—Boyle Fredrickson S.C.

(57) ABSTRACT

An electrode array allows for rapid ablation of a strip of tissue in an organ providing a barrier to blood loss during resection operations.

9 Claims, 6 Drawing Sheets

ELECTRODE ARRAY FOR TISSUE ABLATION

STATEMENT REGARDING FEDERALLY SPONSORED RESEARCH OR DEVELOPMENT

This invention was made with United States Government Support awarded by the following agencies: Grant NIH 5 RO1 DK58839-02. The United States has certain rights in this invention.

CROSS REFERENCE TO RELATED APPLICATIONS

BACKGROUND OF THE INVENTION

The present invention relates to radio frequency (RF) ablation of tissue and in particular to an apparatus using ablation to control bleeding during the resection of a portion of an organ.

The liver is a common site for both primary and metastatic cancer. Surgical resection (hepatectomy) is currently the preferred treatment for liver cancer. During resection, the surgeon typically removes a lobe of the liver, a time consuming procedure where the surgeon must cut through tissue while avoiding or closing large blood vessels. Blood loss during this procedure can adversely affect patient survival, increase hospital stay, and increase complication rates.

Some studies have investigated the use of radio RF ablation or microwave (MW) ablation to coagulate tissue before resection. Henceforth, both RF and MW ablation will be referred to collectively as RF ablation.

In RF ablation, an electrode is inserted into the tissue and current passing from the electrode through the patient to a large area ground pad on the patient's skin coagulates the tissue near the electrode through resistive heating, sealing it against blood flow. In order to ablate the necessary area of tissue, the electrode is removed and reapplied at a series of locations along the tissue slice. The time required for this procedure is generally too long for clinic practice.

BRIEF SUMMARY OF THE INVENTION

The present invention provides an electrode array which may more rapidly ablate an area of tissue to staunch blood flow during resection. The shape of the individual electrodes of the array and their separation is adjusted to reduce insertion force while providing a sufficient area for partitioning. A switching of electricity between the electrodes provides rapid ablation of a tissue slice.

Specifically, the present invention provides an electrode array for RF ablation having a set of elongate electrodes for insertion through tissue of an organ. A holder or guide positions the electrodes with respect to each other to define a surface partitioning the organ.

It is thus one object of at least one embodiment of the invention to provide an electrode assembly that allows for rapid ablation of a slice through an organ to reduce blood loss during resection of a portion of the organ.

It is another object of at least one embodiment of the invention to provide a method for rapidly positioning electrodes for this purpose that may be practical in clinical application.

It is yet another object of at least one embodiment of the invention to enforce an optimized separation and orientation of the electrodes during this procedure.

The electrodes may be flat blades having their flat surfaces parallel.

It is an object of at least one embodiment of the invention to provide an electrode shape which preferentially creates a thin slice of ablated tissue by providing increased surface area facing other electrodes thereby concentrating the heating between electrodes It is another object of at least one embodiment of the invention to provide an electrode shape which reduces insertion forces on the electrodes for a given electrode cross-sectional area.

The elongate electrodes may be separately inserted, sliding along their length through the holder.

It is thus another object of at least one embodiment of the invention to provide a system in which the electrodes may be individually inserted into the organ thus reducing the instantaneous force placed on the organ.

The elongate electrodes may be fixed within the holder.

Thus, it is another object of an alternative embodiment of the invention to allow the electrodes to be simply and rapidly inserted in unison.

The elongate electrodes may be substantially straight and the holder may separate the elongate electrodes along a line so that the elongate electrodes define a plane surface within the organ. Alternatively, the electrode holder may separate the electrodes along a curve so that the elongate electrodes define a curved cylindrical surface within the organ. Alternatively or in addition, the elongate electrodes may be curved so that the elongate electrodes define a curved spherical surface within the organ.

Thus, it is another object of at least one embodiment of the invention to provide an electrode system that may accurately define an ablation region having a variety of shapes.

Each elongate electrode may be affixed to a flexible conductor conducting RF power independently to the elongate electrode.

Thus, it is another object of at least one embodiment of the invention to provide an electrode that allows for sophisticated control of electrode energy to produce a uniform ablation region.

The elongate electrodes may be removable from the holder and the holder may incorporate connectors joining flexible conductors to the elongate electrodes when they are inserted in the holder.

Thus, it is another object of at least one embodiment of the invention to eliminate the need for the surgeon to manage multiple connectors when using the present invention.

The elongate electrodes may slide within the holder and the holder may incorporate slide contact connectors joining the flexible conductors to the elongate electrodes.

Thus, it is another object of at least one embodiment of the invention to provide an electrical connection system that accommodates insertion of the electrodes into the organ at different distances.

The electrode may include thermal sensors for detecting a temperature of tissue around the elongate electrodes. Each of the elongate electrodes may alternatively or in addition include at least two electrically independent zones along their length allowing independent application of electrical power to the zones. Each of these zones may provide a separate thermal sensor.

Thus, it is another object of at least one embodiment of the invention to provide for sophisticated feedback control and sophisticated localized application of power to provide a uniform ablation region in the presence of different tissue characteristics.

Each of the elongate electrodes may include graduations indicating a length along the elongate electrode.

Thus, it is another object of at least one embodiment of the invention to provide electrodes that may be accurately inserted to predetermined depths.

The electrodes may include stops that may be preset to particular depths or a backer sheet that will stop further travel of the electrodes once it has passed through the organ and confronted the backer sheet placed beneath the organ.

Thus, it is another object of at least one embodiment of the invention to provide a method of allowing complete insertion of the electrodes through the organ with minimal risk to underlying tissue.

The RF power may be applied between the electrodes in bipolar fashion.

Thus, it is another object of at least one embodiment of the invention to provide improved slice ablation by confining the electrical flow largely to the plane of the electrodes.

The RF power may be applied to one pair of electrodes at a time.

It is thus another object of at least one embodiment of the invention to provide an ablation system that does not over tax the current output of a conventional RF ablation device.

The particular pair of electrodes between which power flows may be changed on a periodic basis.

Thus, it is another object of at least one embodiment of the invention to provide control of ablation throughout the slice defined by the electrodes.

These particular objects and advantages may apply to only some embodiments falling within the claims and thus do not define the scope of the invention.

DETAILED DESCRIPTION OF THE PREFERRED EMBODIMENT

Figure 1:
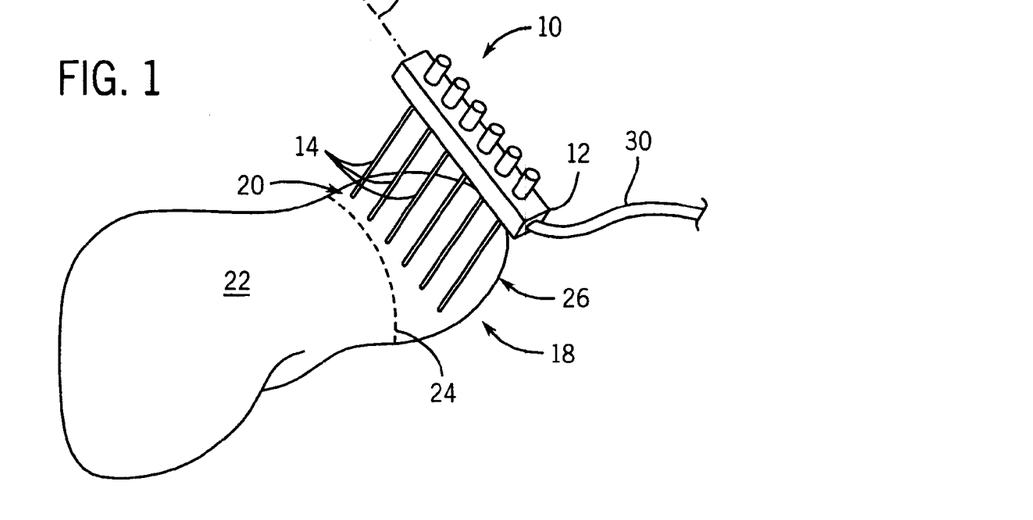
FIG. 1 is a perspective view of a liver showing positioning of the electrode array of the present invention for insertion into the liver for creating an ablated partition in a first embodiment having fixed electrodes.

Referring now to FIG. 1, an electrode array assembly 10 of the present invention includes a holder 12 supporting a number of elongate electrodes 14 spaced along an axis 16 to define a generally planar surface 18 among them. The surface 18, for example, may be 8 cm long and 10 cm wide.

Sharpened tips 20 of the elongate electrodes 14 may be inserted into the liver 22 at an insertion line 24 to isolate one lobe 26 of the liver 22 for resection. The elongate electrodes 14 may, for example, be constructed of a biocompatible stainless steel.

The holder 12 may be, for example, an insulating plastic block having holes cut in the holder 12 to receive metallic shafts of the elongate electrodes 14 at regular intervals. In a preferred embodiment, the separation of the electrodes is approximately 1.5 cm. The elongate electrodes 14 may be fixed to the holder 12 so as to be moved in unison for rapid insertion. Each elongate electrode 14 may be independently attached to a separate conductor 23 (not shown in FIG. 2) of a cable 30 providing independently controllable RF power to each of the elongate electrodes 14 as will be described below.

Figure 2:
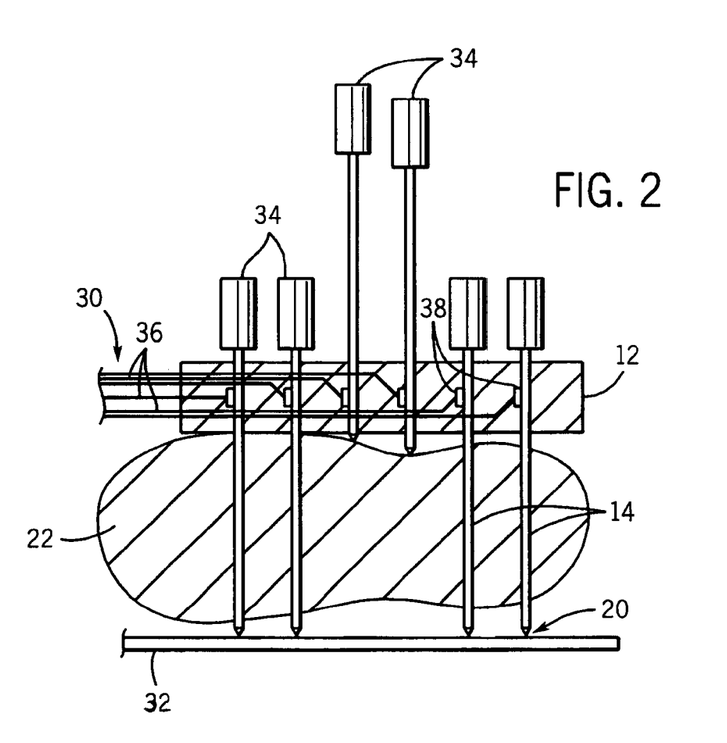
FIG. 2 is a cross-sectional view through the liver after insertion of the electrodes against a stopper plate in a second embodiment having sliding electrodes and electrode connectors.

Referring now to FIG. 2 in an alternative embodiment, each elongate electrode 14 may be separately slidable within the holder 12 as gripped by handles 34 on ends of the elongate electrodes opposite the sharpened tips 20. Separate conductors 36 of the cable 30 may pass to sliding contacts 38 allowing electrical connection to the elongate electrodes 14 throughout their range of travel through the holder 12. In this embodiment, the holder 12 is placed against the liver 22 along insertion line 24 (as shown in FIG. 1) and the individual elongate electrodes 14 are inserted one at a time providing a reduced instantaneous force to be applied to the liver 22. The sliding contacts 38 allow the depth of insertion of the elongate electrodes 14 to be varied freely. A flexible plastic backer sheet 32 may be placed under the liver 22. Insertion of the elongate electrodes 14 through the liver 22 may be stopped by the backer sheet 32 ensuring their full extent through the liver 22 without significant incursion into underlying tissue. In this case, the elongate electrodes 14 may be removable from the holder 12 or may be held in slidable configuration but captive within the holder 12 to prevent the components from being separated.

The backer sheet 32 may also be used with the embodiment of FIG. 1.

Figure 3:
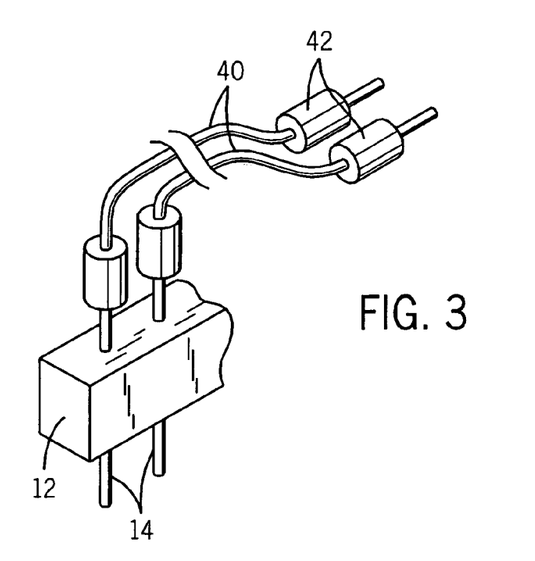
FIG. 3 is a fragmentary view of the holder of the electrodes of FIG. 2 showing an alternative electrical connection method using individual cables attached to each electrode.

Referring now to FIG. 3, the sliding contacts 38 of FIG. 2 may be eliminated in favor of separate cables 40 attached to each elongate electrode 14 and terminating in connectors 42 such as may be connected directly to a source of RF power or to a connector block on the holder 12 (not shown) which may in turn communicate through a cable 30 with the source of RF power. Separate cables 40 may also be used with the embodiment of FIG. 1.

Figure 4:
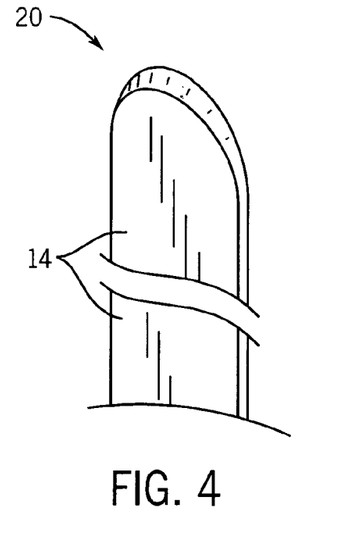
FIG. 4 is a fragmentary detailed perspective view of a sharpened end of one electrode of FIG. 2 showing a blade configuration with a rounded end.

Referring now to FIG. 4, while conventional needle electrodes having a cylindrical cross-section may be used for the elongate electrodes 14 in a preferred embodiment, the elongate electrodes 14 are flattened blades. The tips 20 of the blade elongate electrodes 14 may have a rounded profile with a sharpened peripheral edge to reduce the force of insertion into the liver 22. Alternatively, referring to FIG. 5, the tips 20 of the blade elongate electrodes 14 may have a chisel point leading to a sharpened apex, again with a sharpened peripheral edge. RF power may be applied during insertion of the electrode, to reduce required insertion force and limit bleeding during the insertion.

Figure 5:
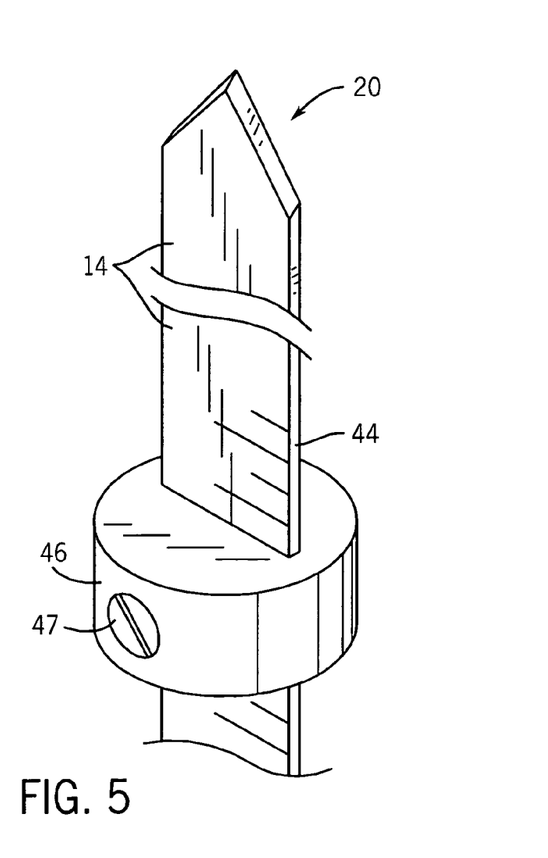
FIG. 5 is a figure similar to that of FIG. 4 showing an alternative embodiment of the blade of FIG. 4 showing a blade configuration with a pointed end and further showing graduation marks on the length of the electrode together with an electrode stop used for controlling insertion depth.

The side of the elongate electrode 14 may include graduations 44 allowing visible control of the depth of the elongate electrode 14. These graduation marks may be used alone or to set a stop 46 using a set screw 47 or the like that attaches to the elongate electrode 14 at any of a range of locations along the side of the elongate electrode 14 so that the depth of the elongate electrode 14 may be reached accurately and quickly.

The handles 34 may be numbered or colored so as to provide for a particular ordering of insertion into the holder 12, in the case when depth has been preset by stops 46, so that the correct elongate electrodes 14 may be inserted appropriately in the holder 12.

Figure 6:
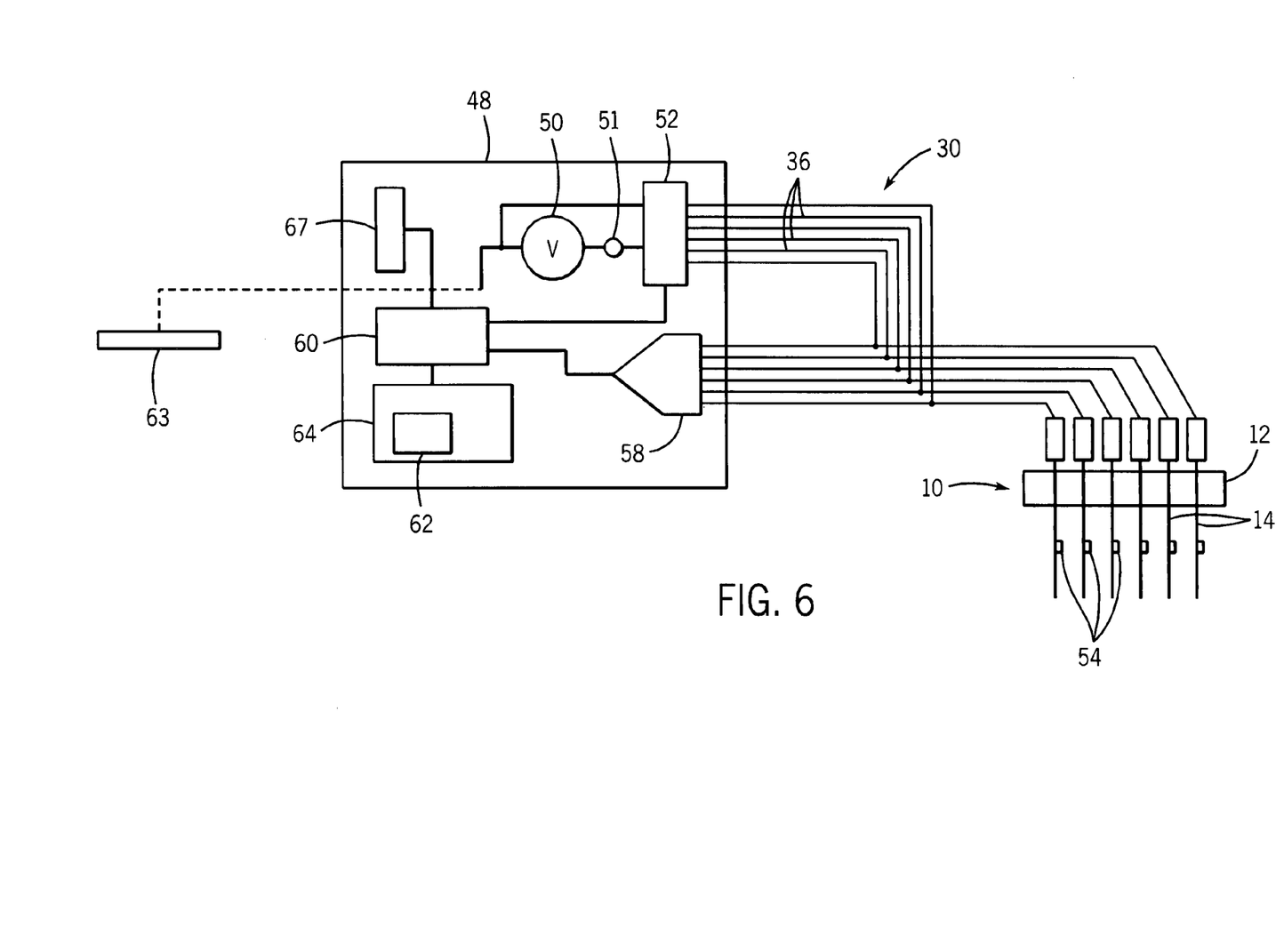
FIG. 6 is a simplified block diagram of a RF power supply suitable for use with the present invention as connected to the electrodes.

Referring now to FIG. 6, the electrode array assembly 10 may be used in conjunction with a power unit 48 providing an RF power source 50. The power unit 48 provides power to the elongate electrodes 14 via an electronically controllable switching circuit 52 communicating with the multiple conductors 36 of cable 30 (or cables 40) passing to the elongate electrodes 14. RF power sources 50 suitable for multiple electrodes are described in U.S. application Ser. No. 10/796,239 filed Mar. 9, 2004 and entitled Multipolar Electrode System for Volumetric Radio Frequency Ablation and U.S. application Ser. No. 10/11,681 filed Jun. 10, 2002 and entitled: Radio-Frequency Ablation System Using Multiple Electrodes, both hereby incorporated by reference.

The power unit 48 may also receive signals from each of the elongate electrodes 14 from an optional thermal sensor 54, such as a thermocouple or solid-state temperature sensor, attached to the surface of the elongate electrodes 14 or within the electrodes. Signals from these thermal sensors 54 may be received by the power unit at input circuit 58 which digitizes and samples the temperature signals and provides them to a microprocessor 60.

The microprocessor 60 executes a stored program 62 held in a memory 64 and also communicates with a front panel control set 67 to provide data to a user and accept user input commands.

While the present invention contemplates that power will be applied to the elongate electrodes 14 in a bipolar mode as will be described, power unit 48 may alternatively communicate with a ground pad 63 to allow monopolar operation.

Figure 7:
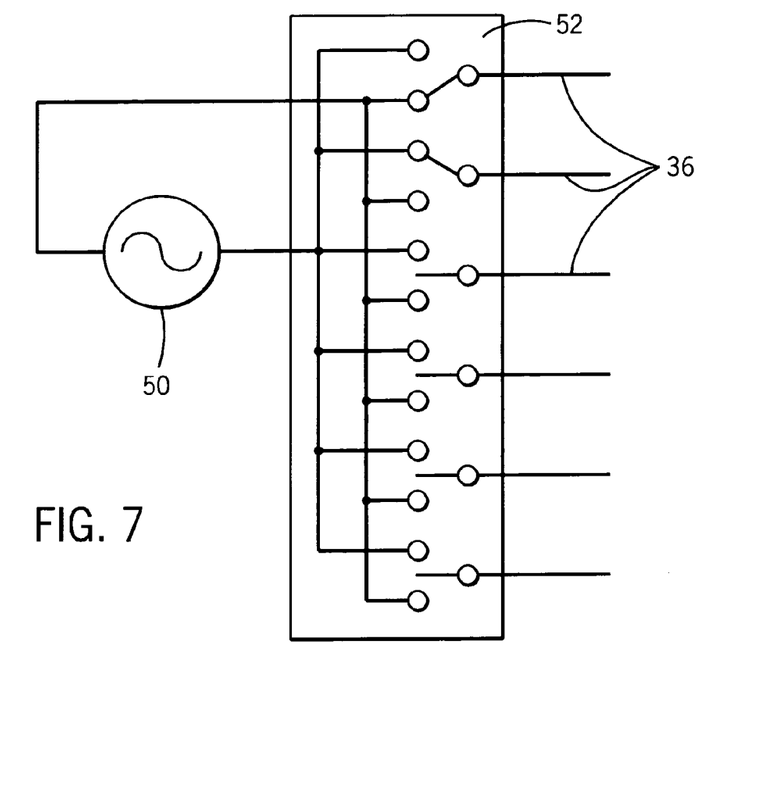
FIG. 7 is a block diagram with a switching circuit used with the power supply of FIG. 6.

Referring now to FIG. 7, the switching circuit 52 provides solid-state switches that allow each conductor 36 attached to an elongate electrode 14 to be switched to either terminal of the RF power source 50 so that the elongate electrode 14 provides either a return or source of RF power. Switching circuit 52 may also be used to disconnect particular ones of the conductors 36 so as to isolate the associated elongate electrode 14 and to allow a duty cycle modulated control of the power going to each elongate electrode 14. Thus, while the power source 50 may optionally run at a constant rate control of the power may be obtained through the switching circuit 52. The switching circuit 52 is connected to the microprocessor 60 to be controlled thereby.

Figure 8:
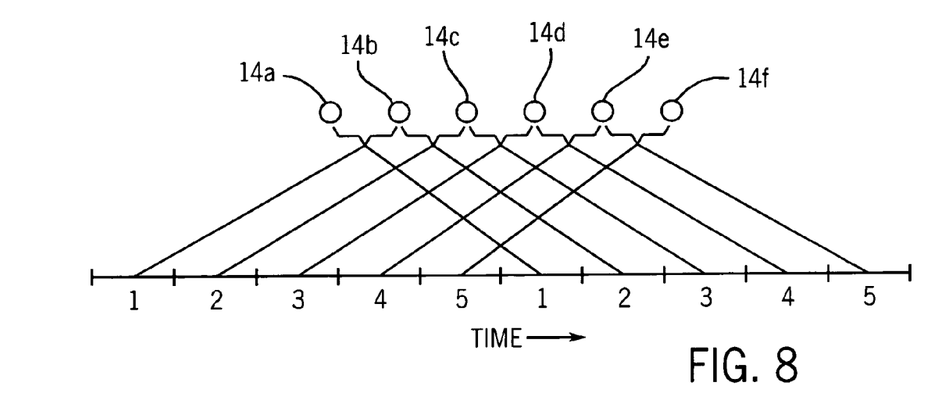
FIG. 8 is a timing diagram showing a sequencing of operation of the switching circuit of FIG. 7 to connect pairs of the electrodes together for bipolar operation.

Referring now to FIG. 8, the microprocessor 60 in a preferred embodiment executes the program 62 in memory 64 to sequentially control the switches of the switching circuit 52 to connect one pair of elongate electrodes 14 to the power source 50 at each time. Accordingly, at a time period 1, a pair of elongate electrodes 14a and 14b will be connected across power source 50 for current to flow therebetween. At this time, all other elongate electrodes 14 are disconnected from the power source 50. At a second time period 2, elongate electrodes 14b and 14c will be connected across the power source 50 for power to flow therebetween and elongate electrode 14a is disconnected from the power source 50.

This process repeats itself for the remaining elongate electrodes 14 until each electrode has been pair-wise connected to the power source 50. After this, the cycle is reinitiated with elongate electrodes 14a and 14b being connected.

In an alternative embodiment, each of the elongate electrodes 14 other than the pair being connected to the power source 50 is connected to a return path so as to provide an effective virtual ground plane for return of current.

In yet another alternative embodiment, the sequential switching of pairs of elongate electrodes 14 does not proceed continuously from left to right but rather every other sequential pairing is skipped to allow cooling of the tissue near each energized electrode before the next adjacent pair is energized. Accordingly, elongate electrodes 14a and 14b may be connected across the power source 50 and then elongate electrodes 14c and 14d, and then elongate electrodes 14e and 14f, and then elongate electrodes 14b and 14c, and then elongate electrodes 14d and 14e and so forth.

As well as limiting the overheating of tissue, the switching of the elongate electrodes 14 provides other benefits. The large number of elongate electrodes 14 may create a very low impedance device which may be beyond the current capability of standard power sources 50. Accordingly, the switched operation also allows that power to be allocated among pairs of the elongate electrodes 14. With standard power sources 50, the ablation region will typically be 1 to 2 cm wide and can be obtained in five to ten minutes. The switching among elongate electrodes 14 may also eliminate shielding effects among electrodes providing a more uniform ablation region.

The amount of power deposited at the tissue surrounding each elongate electrode 14 may be changed by varying the length of the duration of the time periods 1 to 5 as shown in FIG. 8. Alternatively, a high-frequency duty cycle modulation may be imposed on the power applied during the periods 1 to 5 by power source 50 according to well-known techniques.

The control of power deposited at the tissue near each electrode 14 may be controlled by these techniques according to the temperature measured at each elongate electrode 14, for example, to reduce power when the temperature rises above a pre-determined threshold either according to a simple thresholding technique or a more complex feedback loop using proportional, integral, and derivative terms.

As an alternative to temperature control, the impedance of the tissue between each pair of electrodes 14 may be determined by monitoring the current flow into the tissue and the particular voltage of the power source 50 (using an in-line current sensor 51), and this impedance can be used to control power by decreasing, or shutting down power for a certain time period as impedance rises, the latter indicating a heating of the tissue.

Impedance measurements can also be used to gauge the thickness of the tissue being ablated. Referring also to FIG. 2, the tissue may have different thickness in the slice where the electrode array assembly 10 is inserted. By measuring impedance (with low power application of RF current) between adjacent electrodes 14, the slice thickness along the electrodes 14 can be estimated before ablating the slice. Power applied between each electrode pair can then be applied according to tissue thickness (e.g. tissue twice as thick requires twice the power). In one embodiment, this can be achieved by applying a constant voltage bipolar between each electrode pair. If tissue is twice as thick, impedance is about half as great, and as a result the applied power is twice as high with that constant voltage.

Monitoring current and voltage with the microprocessor 60 may also be used to detect excess or low currents to any particular elongate electrode 14. In the former case, power limiting may be imposed. The latter case may indicate a disconnection of one or more elongate electrodes 14 and an indication of this may be provided on the front panel control set 67 to the user.

It will be apparent to those of ordinary skill in the art that a number of other control feedback techniques may be used including those which control current flow or voltage or power (the latter being the product of current and voltage) according to each of these terms.

Figure 13:
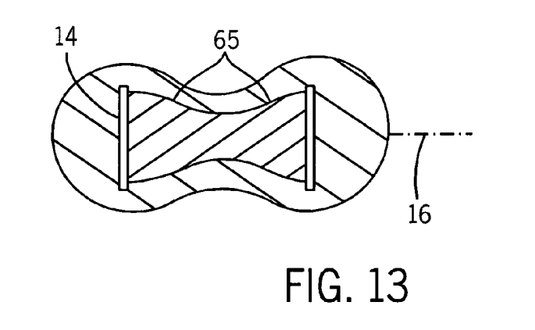
FIG. 13 is a simplified representation of the spacing between two blade electrodes showing the improved ablation zones obtained by the parallel blade structure and bipolar operation.
Figure 14:
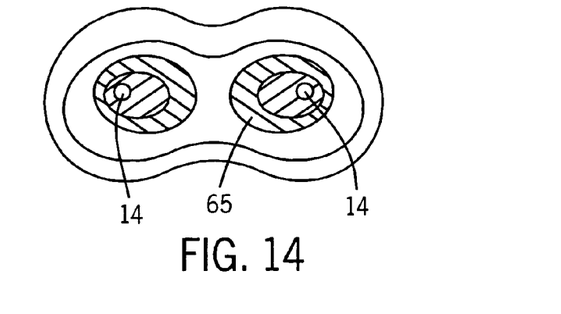
FIG. 14 is a view similar to FIG. 13 showing needle electrodes such as provide asymmetrical ablation regions through the use of bipolar stimulation but which may require closer electrode spacing.

Referring now to FIG. 13, the flat shape of the elongate electrodes 14 provides an asymmetrical ablation region 65 that preferentially ablates tissue along axis 16 allowing increased spacing of elongate electrodes 14 (and thus fewer electrodes and less insertion force) as well as a relative uniform but thin ablation region. In contrast, the use of needle elongate electrodes 14 as shown in FIG. 14 may require closer spacing to obtain a continuous ablation region 65.

Figure 9:
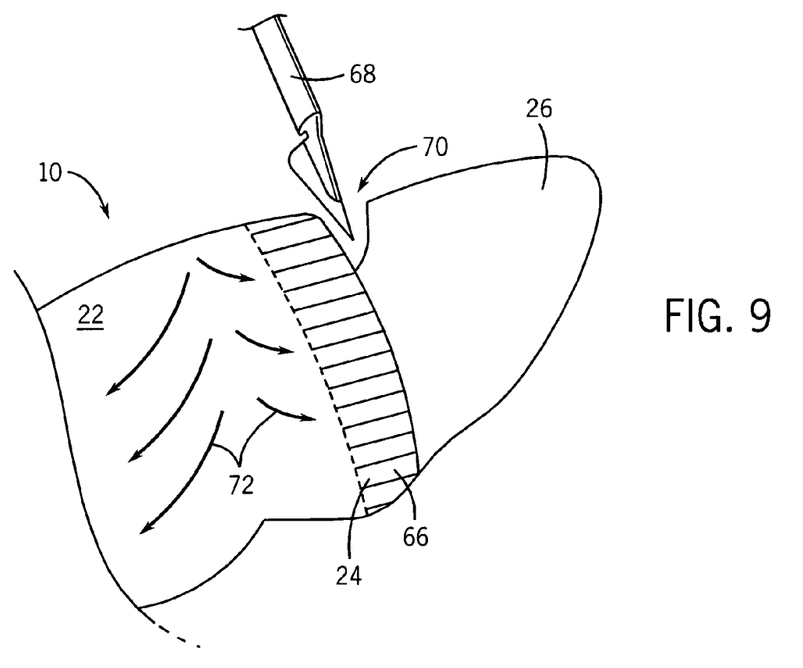
FIG. 9 is a fragmentary perspective view of the liver showing resection of a portion of the tumor after ablation by cutting on an outside edge of the ablation region.

Referring now to FIG. 9, once the liver 22 is ablated along an ablation region 66 intersecting insertion line 24, a scalpel 68 may be used to resect a lobe 26 of the liver 22 by making a cut 70 on the outside of the ablation region 66 with respect to a general path 72 of blood flow through the liver 22. The ablation region 66 thus reduces blood loss during the resection process.

Figure 10:
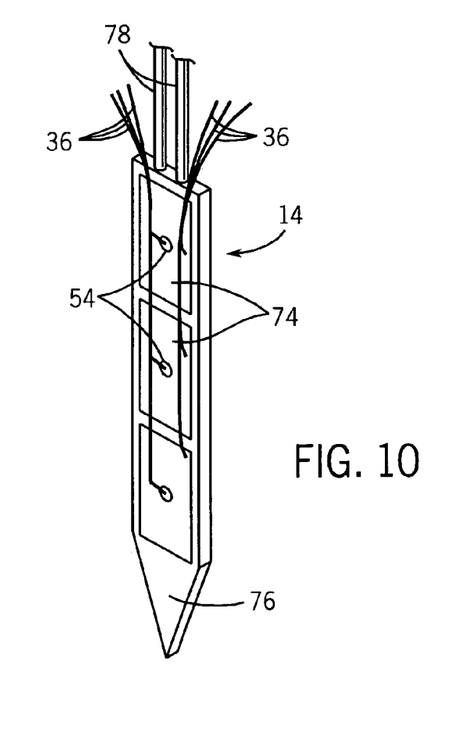
FIG. 10 is an alternative embodiment of the electrode of FIG. 5 having multiple isolated conductive zones and thermal sensors on each zone for independent control of ablation along the length of the electrode.

Referring now to FIG. 10 in an alternative embodiment, elongate electrode 14 may include a number of independently conductive zones 74 separated on an insulating substrate 76. Each conductive zone 74 communicates with a separate conductor 36 so as to allow independent control of current flow into the tissue not simply among elongate electrodes but along the length of each elongate electrode 14. A thermal sensor 54 may be associated with each region further providing independent feedback control of each region.

Referring still to FIG. 10, active cooling of the elongate electrodes 14 may also be accomplished through the use of small pipes 78 through which cooled fluid such as air or liquid may be passed.

Figures 11, 12:
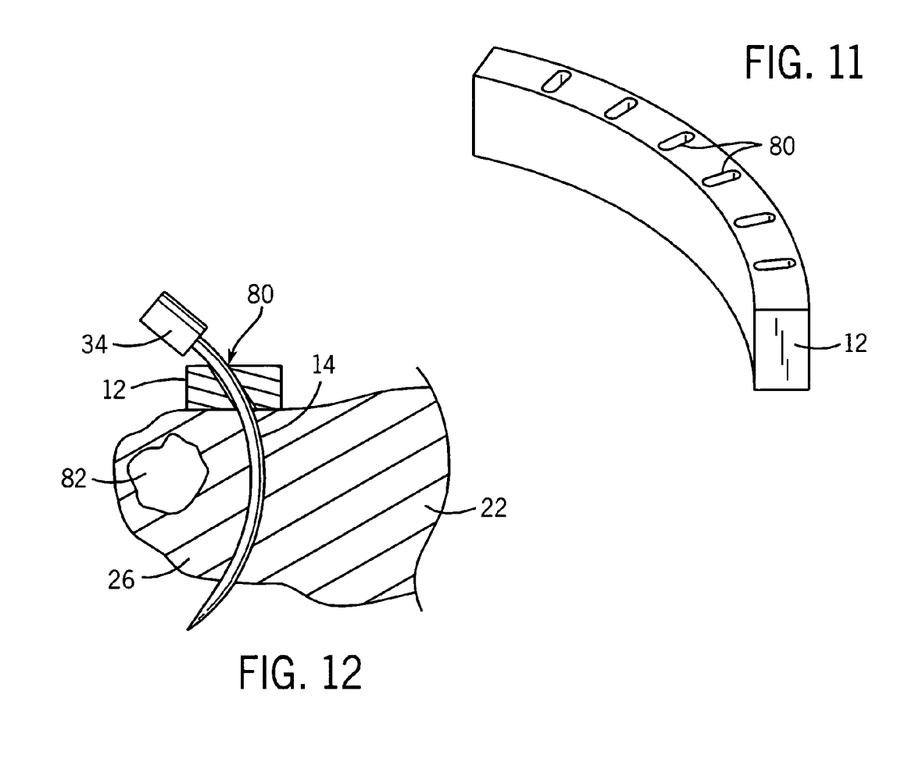
FIG. 11 is an alternative embodiment of the holder of FIG. 1 for providing a curved surface for the ablation region.
FIG. 12 is a cross-sectional view through a liver showing the use of a curved electrode such as may be used with the curved holder FIG. 11 to realize a hemispherical ablation surface or with the straight holder of FIG. 1 to realize a cylindrical ablation surface.

Referring now to FIG. 11 in an alternative embodiment, the holder 12 is not planar, but may have an arcuate shape with holes 80, through which the elongate electrodes 14 are inserted, being arranged along a radius so that the elongate electrodes 14 as positioned by the holder 12 describe a hemi cylindrical surface conforming to an outline, for example, of a tumor in the lobe 26 to be resected.

Referring to FIG. 12, alternatively or in addition, each elongate electrode 14 may be curved so as to fit through an arcuate hole 80 in the holder 12, the holder 12 which may be straight or curved. In the former case, the elongate electrodes provide a hemicylindrical ablation surface having an axis parallel to axis 16 along which the elongate electrodes are separated. In the latter case, the elongate electrodes provide a curved surface in two dimensions approximating a hemispherical surface to conform to a possible tumor region 82 within the lobe 26.

The present invention is not limited to use with the liver 22, but may be used generally in any medical procedure where a barrier needs to be created prior to a cutting of tissue and in particular for surgery in other organs. The switching schedule through which power deposition is controlled may be regular or varied.

It is specifically intended that the present invention not be limited to the embodiments and illustrations contained herein, but include modified forms of those embodiments including portions of the embodiments and combinations of elements of different embodiments as come within the scope of the following claims. For example, the range of RF frequencies used in the present invention may extend from the kilohertz range to microwave frequencies using appropriate electrode structures.

We claim:

1. A method of resecting a portion of an organ comprising the steps of:
    (a) inserting an electrode array into the organ, the electrode array providing a set of elongate electrodes positioned by a holder to a surface along a resection cut line;
    (b) switching radio frequency power to the electrodes to cyclically apply power between different pairs of the electrodes to create a partition of ablated tissue across the cut line; and
    (c) cutting the tissue of the organ at the ablated tissue to reduce blood loss during resection of a portion of the organ;
    wherein the elongate electrodes slide within the holder and include graduation marks and including the steps of:
    (1) positioning the holder against the organ; and
    (2) individually inserting the electrodes into the holder and sliding them different distances guided by the graduation marks so that the electrodes penetrate the organ to different predetermined depths matching thicknesses of the organ.

2. The method of claim 1 wherein the cut positions at least a portion of the ablated tissue between the cut and a region of blood flow into the organ.

3. The method of claim 1 further including placing an electrode stop beneath the organ with respect to the electrode array to stop further travel of the electrodes of the electrode array after the electrodes have passed through the organ.

4. The method of claim 1 wherein the radio frequency is duty cycle modulated to control the application of power to the organ.

5. The method of claim 1 including the step of controlling an average current flow at the electrodes according to at least one parameter selected from the group consisting of: local temperature of the tissue, local impedance of the tissue, a predetermined current limit, and a predetermined power limit.

6. A method of resecting a portion of an organ comprising the steps of:
- (a) inserting an electrode array into the organ, the electrode array providing a set of elongate electrodes positioned by a holder to a surface along a resection cut line;
- (b) switching radio frequency power to the electrodes to cyclically apply power between different pairs of the electrodes to create a partition of ablated tissue across the cut line; and
- (c) cutting the tissue of the organ at the ablated tissue to reduce blood loss during resection of a portion of the organ;

wherein the elongate electrodes slide within the holder and including the steps of:
- (1) based on determined thicknesses of the organ, moving and affixing stops to different locations on the electrodes to control the insertion of the electrodes to different depths to match the thicknesses of the organ;
- (2) positioning the holder against the organ; and
- (3) individually inserting the electrodes into the holder and sliding them through the holder against the stops.

7. The method of claim 6 wherein the cut positions at least a portion of the ablated tissue between the cut and a region of blood flow into the organ.

8. The method of claim 6 wherein the radio frequency is duty cycle modulated to control the application of power to the organ.

9. The method of claim 6 including the step of controlling an average current flow at the electrodes according to at least one parameter selected from the group consisting of: local temperature of the tissue, local impedance of the tissue, a predetermined current limit, and a predetermined power limit.

* * * * *

UNITED STATES PATENT AND TRADEMARK OFFICE
CERTIFICATE OF CORRECTION

PATENT NO. : 7,367,974 B2  
APPLICATION NO. : 10/945380  
DATED : May 6, 2008  
INVENTOR(S) : Dieter Haemmerich et al.

Page 1 of 1

It is certified that error appears in the above-identified patent and that said Letters Patent is hereby corrected as shown below:

In the Specification

Column 1, Lines 7-10:
Delete the phrase:
"This invention was made with United States Government Support awarded by the following agencies: Grant NIH 5 RO1 DK58839-02. The United States has certain rights in this invention."
And replace with:
--This invention was made with government support under DK058839 awarded by the National Institutes of Health. The government has certain rights in the invention.--.

Signed and Sealed this
Eighth Day of December, 2020

Andrei Iancu
*Director of the United States Patent and Trademark Office*